United States Patent [19]

Yanagawa et al.

[11] Patent Number: 4,860,758
[45] Date of Patent: Aug. 29, 1989

[54] MULTIPLE DIAGNOSABLE DISTANCE RANGE ULTRASONIC DIAGNOSTIC APPARATUS

[75] Inventors: Yutaka Yanagawa; Akira Taniguchi, both of Tokyo, Japan

[73] Assignee: Olympus Optical Co. Ltd., Tokyo, Japan

[21] Appl. No.: 85,547

[22] Filed: Aug. 14, 1987

[30] Foreign Application Priority Data

Aug. 14, 1986 [JP] Japan .................. 61-190925
Aug. 14, 1986 [JP] Japan .................. 61-190926
Aug. 28, 1986 [JP] Japan .................. 61-202081

[51] Int. Cl.$^4$ ................................ A61B 8/12
[52] U.S. Cl. .................. 128/662.06; 128/660.10
[58] Field of Search .................. 128/660–661, 128/662.06, 660.10; 73/625–626, 618–620, 642, 644

[56] References Cited

U.S. PATENT DOCUMENTS

| | | | |
|---|---|---|---|
| 3,817,089 | 6/1974 | Eggleton et al. | 128/661 X |
| 3,938,502 | 2/1976 | Bom | 128/661 X |
| 4,137,777 | 2/1979 | Haverl et al. | 128/660 X |
| 4,161,121 | 7/1979 | Zitelli et al. | 128/660 X |
| 4,161,122 | 7/1979 | Buchner | 128/660 |
| 4,233,988 | 11/1980 | Dick et al. | 73/642 X |
| 4,242,911 | 1/1981 | Martin | 73/626 X |
| 4,253,338 | 3/1981 | Iinum et al. | 736/626 |
| 4,462,092 | 7/1984 | Kawabuchi et al. | 128/660 X |
| 4,541,435 | 9/1985 | Saito et al. | 128/660 |
| 4,605,009 | 8/1986 | Pourcelot et al. | 128/660 |
| 4,708,127 | 11/1987 | Abdelghani | 128/24 A |

FOREIGN PATENT DOCUMENTS

| | | | |
|---|---|---|---|
| 61-11026 | 1/1986 | Japan | 128/660.01 |
| 61-37145 | 2/1986 | Japan | 128/660.01 |

*Primary Examiner*—Francis Jaworski
*Attorney, Agent, or Firm*—Ladas & Parry

[57] ABSTRACT

First and second ultrasonic transducers are provided at the distal end portion of a flexible insertion portion (to serve as a probe) of an endoscope. During diagnosis, the distal end portion of insertion portion is fixed in a tubular organ by a balloon which is filled with water. Ultrasonic lenses having different focal distances are mounted on the transducers. The resonance frequencies of the transducers differ from each other. The transducers are rotated about a shaft of the insertion portion by a motor, in order to mechanically radial-scan an object to be examined. A relay box for supplying a drive signal to the transducers is connected to the endoscope, and a diagnositc device with a display is connected to the relay box. The relay box includes first and second transmitting circuits, and output drive pulses therefrom are supplied to the transducers. The relay box also comprises a switch and a switching circuit connected to the transmitting circuits for selecting one of the transmitting circuits by operating the switch. Therefore, only a selected one of the transmitting circuits supplies the drive pulse to the transducer. An ultrasonic echo signal received by the transducer is supplied to the diagnostic device to display a tomographic image.

5 Claims, 10 Drawing Sheets

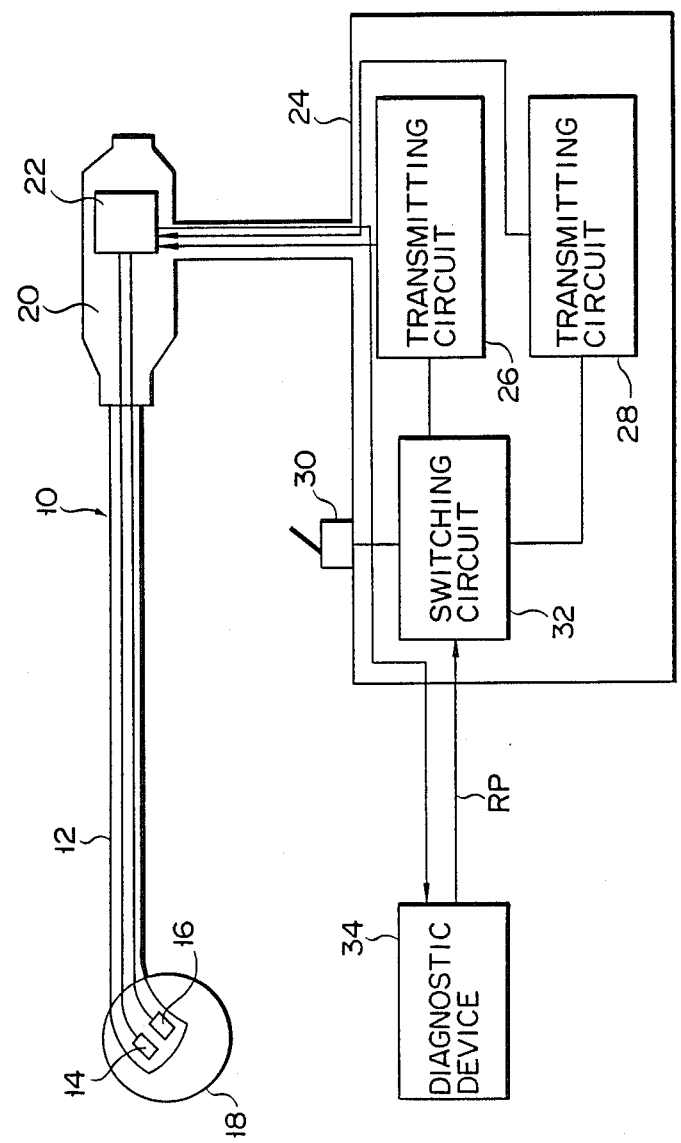
F I G. 1

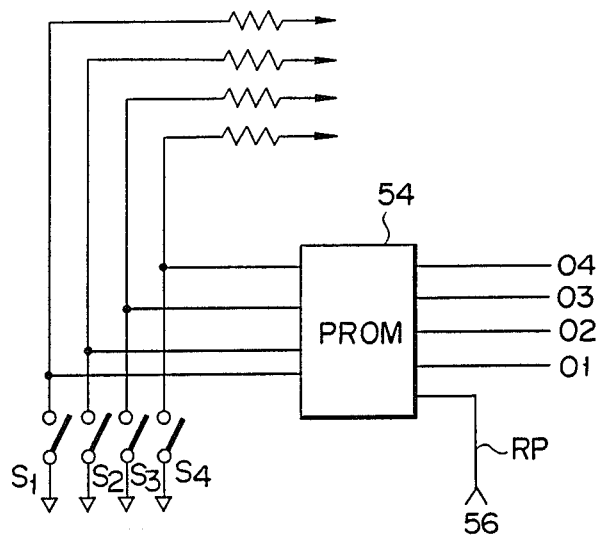
F I G. 4
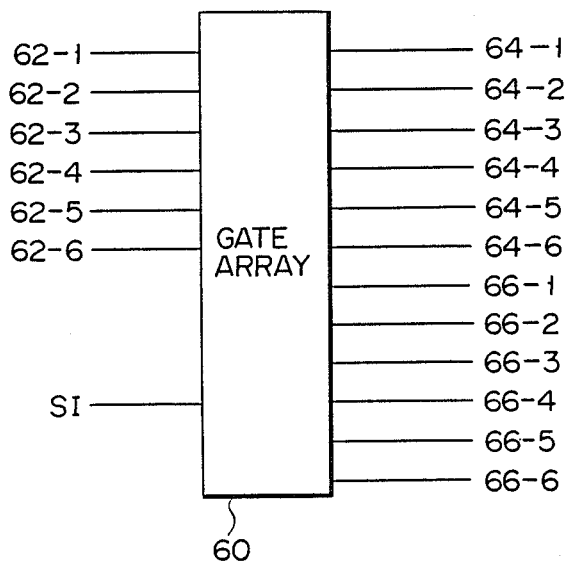
F I G. 5

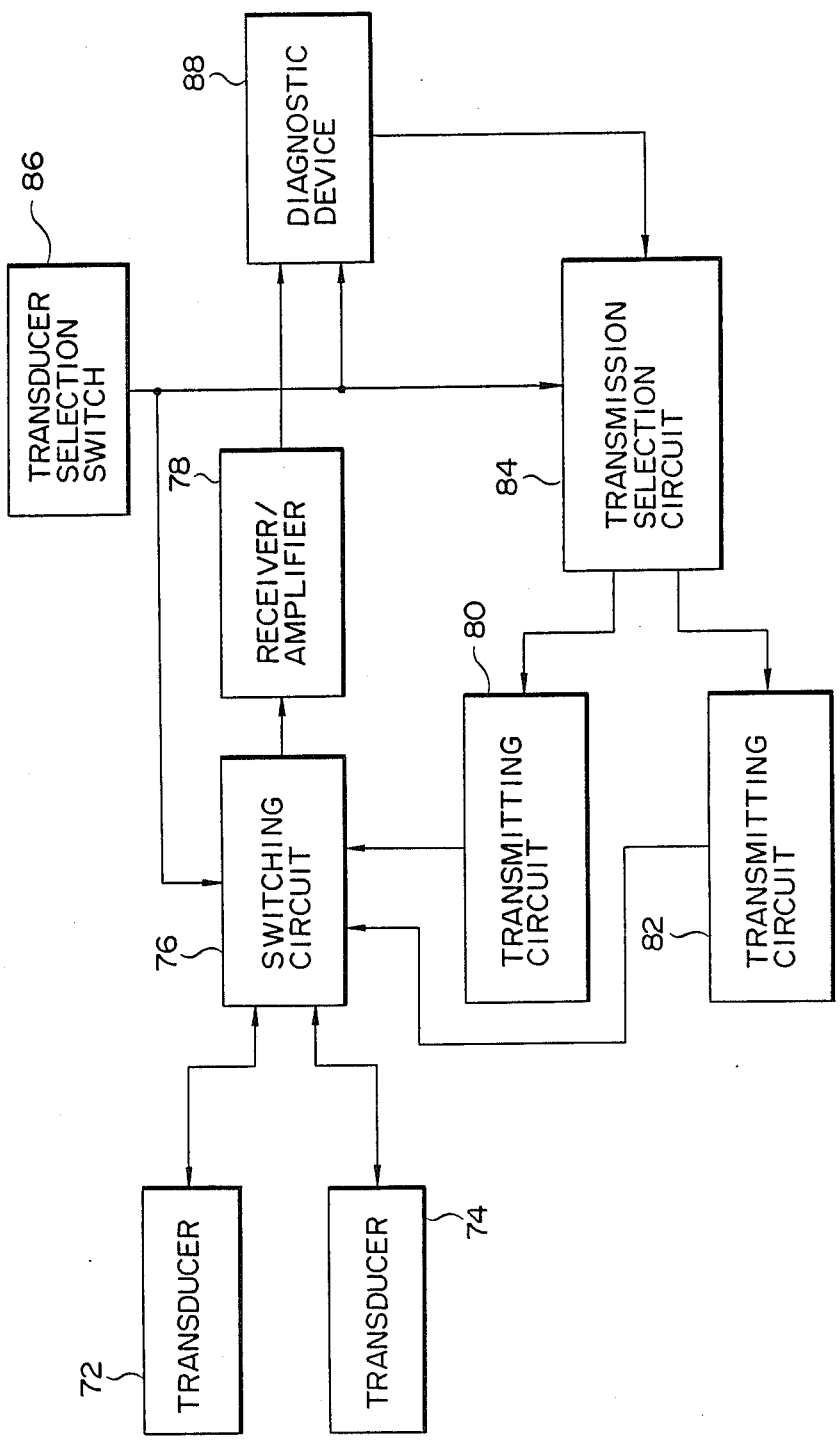
F I G. 7

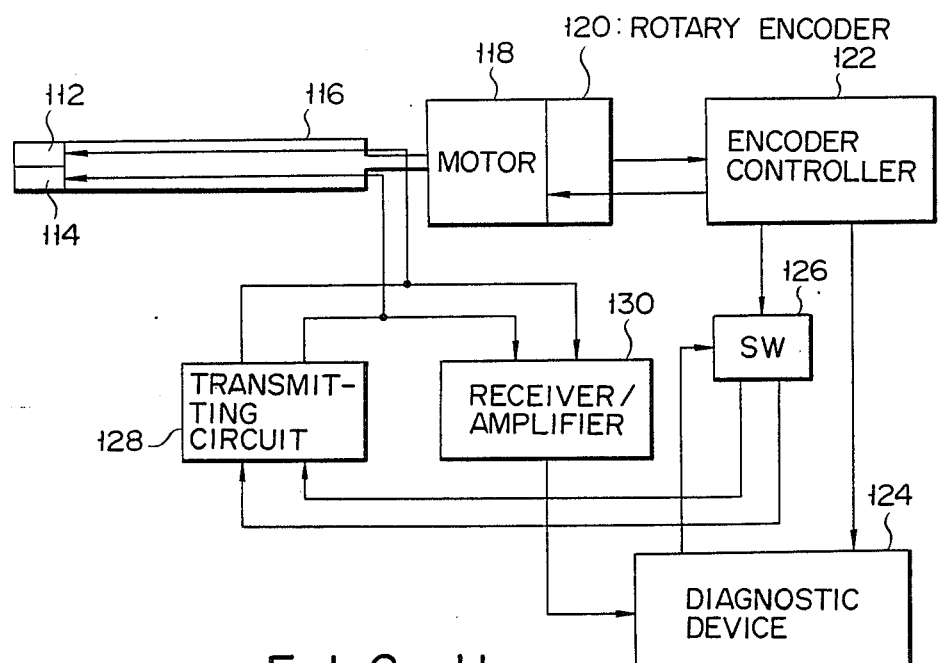
F I G. 11
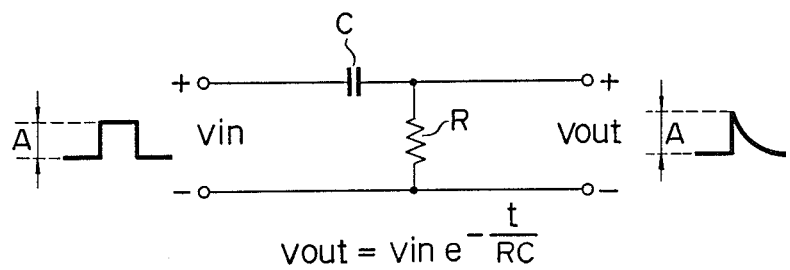
$$v_{out} = v_{in} e^{-\frac{t}{RC}}$$
F I G. 12A
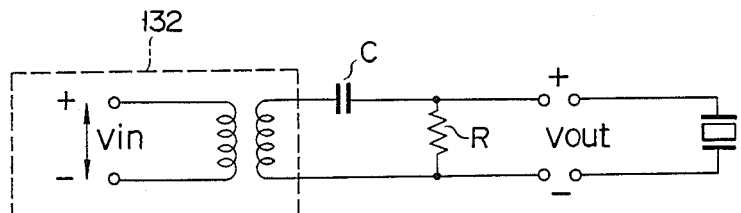
F I G. 12B F I G. 13
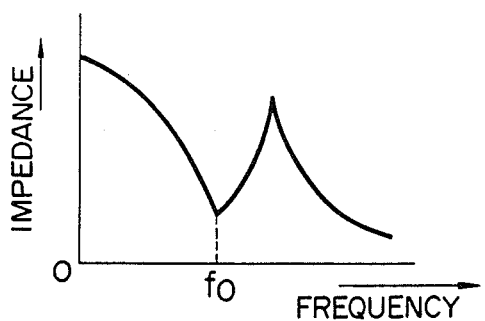
F I G. 14A
(DRIVE PULSE)
F I G. 14B
(TRANSMITTED SIGNAL)
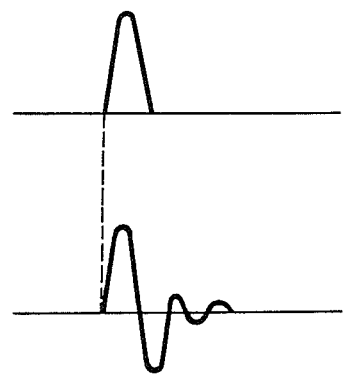
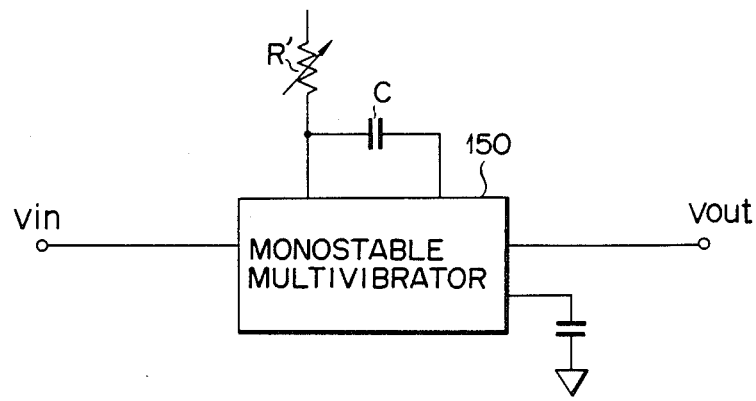
F I G. 15

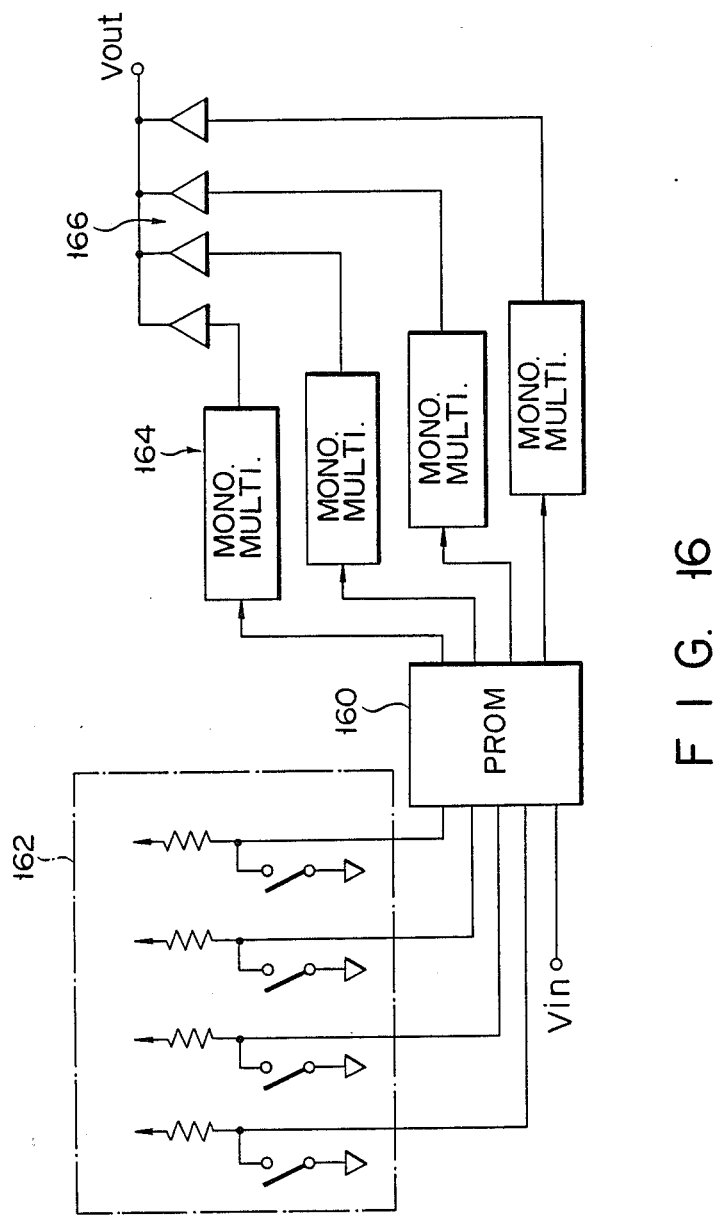
F I G. 16

MULTIPLE DIAGNOSABLE DISTANCE RANGE ULTRASONIC DIAGNOSTIC APPARATUS

BACKGROUND OF THE INVENTION

The present invention relates to an ultrasonic diagnostic apparatus and, more particularly, to an ultrasonic diagnostic apparatus comprising a plurality of ultrasonic transducers having different ultrasonic characteristics. The ultrasonic characteristics include the resonance frequency of the ultrasonic transducer and the focal length of an ultrasonic lens mounted on the ultrasonic transducer.

When a typical ultrasonic diagnostic apparatus is being used, an ultrasonic transducer such as a piezoelectric element is generally positioned close to an object to be examined, a high-frequency AC voltage of a MHz-band equal to a resonance frequency of the transducer is applied to the transducer for an extremely short time period, so that the transducer is resonated, thereby causing it to emit an ultrasonic pulse. In this case, if the object to be examined is a uniform medium, the ultrasonic pulse propagates linearly therethrough. However, if there is a boundary is between tissues having different acoustic impedances, some pulses are reflected thereat, and some are transmitted therethrough. This reflected echo is received by the transducer, and the distance between the transducer and the boundary is measured in accordance with the speed of the ultrasonic wave and the time required for the ultrasonic pulse to reciprocate. When echo signals obtained from one transmitted pulse are aligned, an image signal representing slice information of the tissue along one direction is obtained. In a radial scanning type diagnostic apparatus, the transducer is rotated in a slice of the object to be examined. Therefore, by transmitting the ultrasonic pulses by the transducer n times when the transducer rotates once, an image signal in a scanning line is obtained by dividing a circle at n equal angular intervals, thereby obtaining a tomographic image of the object to be examined.

In this case, the amount of attenuation of the ultrasonic wave varies depending on resonance frequencies, and the distance range in which a clear image is obtained is predetermined also, depending on resonance frequencies. In general, the lower the resonance frequency, the farther the ultrasonic wave propagates. For this reason, in order to obtain a clear image in a wide range, from short to long distances, the total distance is divided into a plurality of short distances, and a transducer having an optimal resonance frequency is assigned to each short distance; i.e., a plurality of transducers must be provided.

Such a conventional ultrasonic diagnostic apparatus is disclosed in Japanese Patent Disclosure (Kokai) No. 61-11026. This apparatus comprises a probe having at its distal end a flexible tube to be freely inserted/extracted with respect to a body cavity, with two ultrasonic transducers having different resonance frequencies being incorporated in the distal end of the tube.

In this apparatus, in order to display an image in real time, by synthesizing close and remote images respectively obtained from the two transducers which are simultaneously driven, the frame rate must be decreased to ½. For this reason, this apparatus is not suitable for use in the diagnosis of a rapidly moving portion, e.g., the heart.

In addition, since a special synthesizing circuit is required to synthesize two images, the circuit arrangement is therefore complicated.

Furthermore, an ultrasonic echo signal from one of the transducers is undesirably superposed as noise on that from the other transducer. Additionally, when the resonance frequencies of the two transducers are different, if a frequency of a transmitted signal is matched with one of the transducers for the sake of simplicity of the device, the sensitivity is degraded because the frequency differs from the resonance frequency of the other transducer.

An external ultrasonic diagnostic apparatus has drawbacks similar to those of an internal ultrasonic diagnostic apparatus.

In addition, the probe comprising the ultrasonic transducers is generally independent from an electrical circuit portion for applying a drive signal (high-frequency AC voltage) to the ultrasonic transducers and for forming an image signal from an echo signal reflected by the transducers. The time required for applying the high-frequency AC voltage to the transducers, so as to transmit the ultrasonic pulse, varies in accordance with the respective resonance frequencies. However, since the electrical circuit portion is expensive, a single electrical circuit portion is used for the two transducers in the apparatus disclosed in the above reference. For this reason, in accordance with the type of transducer connected thereto, the high-frequency AC voltage cannot be applied to the ultrasonic transducers within an optimal time interval. If the ultrasonic transducer is not driven for a time according to the resonance frequency, vibration of a mode other than the mode of vibration in the direction of thickness, e.g., the mode of vibration in the lateral direction or longitudinal direction or distortion vibration will be generated.

A conventional example for solving the above drawbacks is disclosed in Japanese Patent Disclosure (Kokai) No. 61-37145. In this apparatus, the frequency of a transmitted pulse can be selected from among a plurality of frequencies. However, in this conventional example, since a plurality of types of transmitted pulses having different frequencies are generated and one of them is selected in accordance with the type of transducer, useless transmitted pulses are generated, and the circuit cannot be made compact.

SUMMARY OF THE INVENTION

It is, therefore, an object of the present invention to provide an ultrasonic diagnostic apparatus comprising a plurality of ultrasonic transducers having different diagnosable distance ranges in which S/N ratio is improved by preventing an echo signal from one transducer from being input to another transducer as noise, thereby achieving high sensitivity.

It is another object of the present invention to provide a compact ultrasonic diagnostic apparatus comprising a plurality of ultrasonic transducers, in which a transmitting circuit and a receiving circuit can be simplified.

It is still another object of the present invention to provide an ultrasonic diagnostic apparatus in which if resonance frequencies of ultrasonic transducers connected thereto are different, a drive pulse having an optimal time interval can always be applied to each ultrasonic transducer.

An ultrasonic diagnostic apparatus according to the present invention comprises a plurality of ultrasonic transducers having different ultrasonic characteristics, and a transmitting circuit for supplying a drive signal to only a selected one of the ultrasonic transducers.

In addition, an ultrasonic diagnostic apparatus according to the present invention comprises a plurality of ultrasonic transducers having different ultrasonic characteristics, a transmitting circuit for supplying a drive signal to only a selected one of the ultrasonic transducers, and a receiving circuit for processing a received signal from only the selected one of the ultrasonic transducers to generate an image signal.

Further more, an ultrasonic diagnostic apparatus according to the present invention comprises a plurality of ultrasonic transducers scanned at a predetermined cycle and having different ultrasonic characteristics, a circuit for periodically generating a drive pulse having a constant pulse width in synchronism with scanning of the ultrasonic transducer, and a transmitting circuit for adjusting a pulse width of the drive pulse in accordance with a resonance frequency of a selected one of the ultrasonic transducers, and for applying the drive pulse to the selected one of the ultrasonic transducers.

BRIEF DESCRIPTION OF THE DRAWINGS

FIG. 1 is a block diagram of a first embodiment of an ultrasonic diagnostic apparatus according to the present invention;

FIG. 4 is a circuit diagram of a modification of the switching circuit of the first embodiment;

FIG. 5 is a circuit diagram of another modification of the switching circuit of the first embodiment;

FIG. 7 is a block diagram of a second embodiment of an ultrasonic diagnostic apparatus according to the present invention;

FIG. 11 is a block diagram of a third embodiment of an ultrasonic diagnostic apparatus according to the present invention;

FIGS. 12A and 12B are circuit diagrams of a transmitting circuit of the third embodiment;

FIG. 13 is a graph of a general impedance characteristic of an ultrasonic transducer;

FIGS. 14A and 14B are views of general input/output characteristics of an ultrasonic transducer;

FIG. 15 is a circuit diagram of a modification of the transmitting circuit of the third embodiment; and FIG. 16 is a circuit diagram of another modification of the transmitting circuit of the third embodiment.

DETAILED DESCRIPTION OF THE PREFERRED EMBODIMENTS

Figure 2:
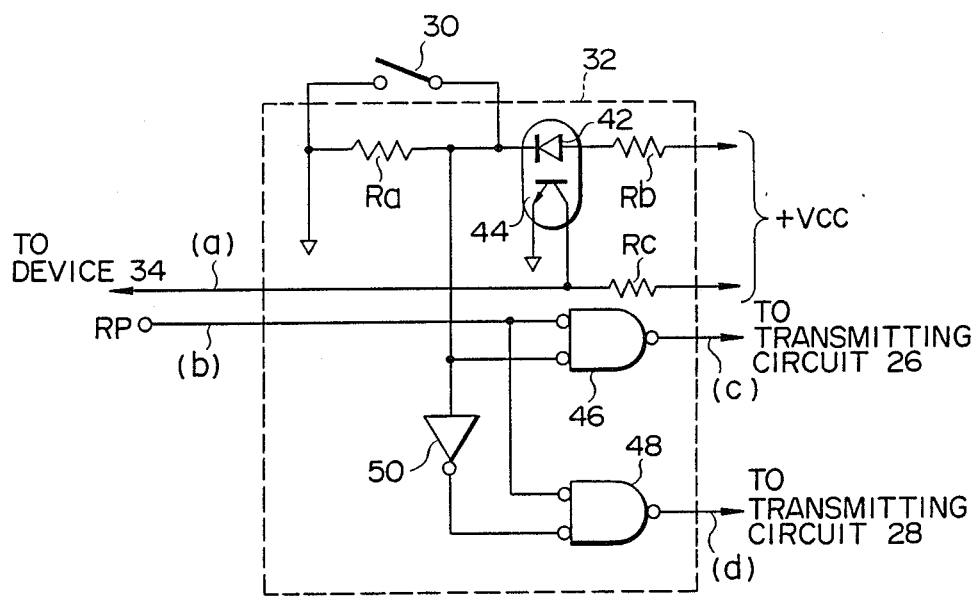
FIG. 2 is a circuit diagram of a switching circuit of the first embodiment.

Embodiments of an ultrasonic diagnostic apparatus according to the present invention will be described below with reference to the accompanying drawings.

FIG. 1 is a block diagram of a first embodiment of the present invention. Although external and internal ultrasonic diagnostic apparatuses are available, a description in the first embodiment will be made by exemplifying an internal ultrasonic diagnostic apparatus in which an ultrasonic probe is inserted in a body cavity. However, the present invention can be similarly applied to an external ultrasonic diagnostic apparatus.

In this embodiment, flexible insertion portion 12 of endoscope 10 is used as a probe, and first and second ultrasonic transducers 14 and 16 are provided at the distal end portion of insertion portion 12. As an endoscope, a conventional fiber scope having an image guide and a light guide may be used, and a recently developed so-called electronic scope incorporating a solid-state imaging element such as a CCD at its distal end portion may also be used. During diagnosis, the distal end portion of insertion portion 12 is fixed in a tube-like organ by balloon 18 which is full of water.

Ultrasonic lenses (not shown) having different focal lengths are mounted on transducers 14 and 16. For example, a focal point of an ultrasonic wave from transducer 14 is closer than that from transducer 16. In addition, resonance frequencies of transducers 14 and 16 are also different.

Transducers 14 and 16 are rotated about a shaft of insertion portion 12 by a motor (not shown). That is, transducers 14 and 16 mechanically radial-scan an object to be examined. This scanning method is merely an example, and electronic linear scanning or electronic sector scanning may be used.

Relay circuit board 22 is provided in hand operating portion 20 of endoscope 10. Circuit board 22 is provided as a relay for signal lines in favor of actual assembly and wiring. In addition, an amplifier for transmitting a weak ultrasonic echo without attenuating it may be arranged on circuit board 22. Relay box 24 for supplying a drive signal (single pulse signal) to the transducer is connected to endoscope 10, and diagnostic device 34 is connected to box 24.

Box 24 comprises first and second transmitting circuits 26 and 28, and output drive signals therefrom are supplied to transducers 14 and 16 through circuit board 22. Box 24 also comprises switch 30 and switching circuit 32 connected thereto, and circuit 32 selects one of circuits 26 and 28 upon operation of switch 30. As a result, only a selected one of circuits 26 and 28 supplies the drive signal to the transducer. Switch 30 may be provided at operating portion 20 of endoscope 10 or at diagnostic device 34. Circuit 32 may be provided in a connector between diagnostic device 34 and box 24. Also, an adapter incorporating circuit 32 may be provided independently of box 24.

Ultrasonic echo signals received by transducers 14 and 16 are supplied to diagnostic device 34 to display a tomographic image.

FIG. 2 is a detailed circuit diagram of circuit 32. Resistor Ra is connected in parallel to switch 30. One terminal of resistor Ra is grounded, and the other terminal thereof is connected to power source Vcc through light-emitting diode 42 of photocoupler 40 and resistor Rb. In this case, Ra >> Rb. The emitter of phototransistor 44 of photocoupler 40 is grounded, the collector thereof is connected to power source Vcc through resistor Rc and also connected to diagnostic device 34.

Circuit 32 also comprises OR gates 46 and 48, and output signals from OR gates 46 and 48 are respectively supplied to circuits 26 and 28. A rate pulse RP supplied from device 34 for determining a transmitting timing of the transducer is connected to the first input terminals of OR gates 46 and 48, the other terminal of resistor Ra is directly connected to the second input terminal of OR gate 46 and is connected to the second input terminal of OR gate 48 through inverter 50.

Figure 3A:
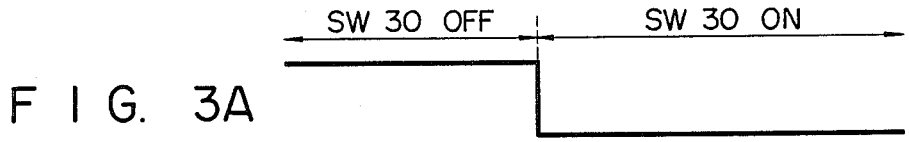
FIGS. 3A, 3B, 3C and 3D are timing charts for explaining an operation of the first embodiment.
Figure 3B:

An operation of the first embodiment will be described below with reference to FIGS. 3A to 3D. A level in the following description is a TTL level. By opening/closing switch 30, one of transducers 14 and 16 is selected. In order to select transducer 16, switch 30 is opened. When switch 30 is open, photodiode 42 is not turned on and hence photocoupler 40 is in a nonconductive state, so that signal (a) supplied to diagnostic device 34 is at high level as shown in FIG. 3A. Diagnostic device 34 displays, in accordance with a level of this signal (a), that transducer 16 is selected.

Figure 3C:
Figure 3D:
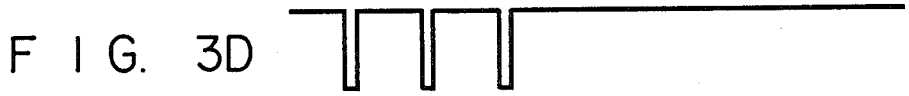
Figure 6:
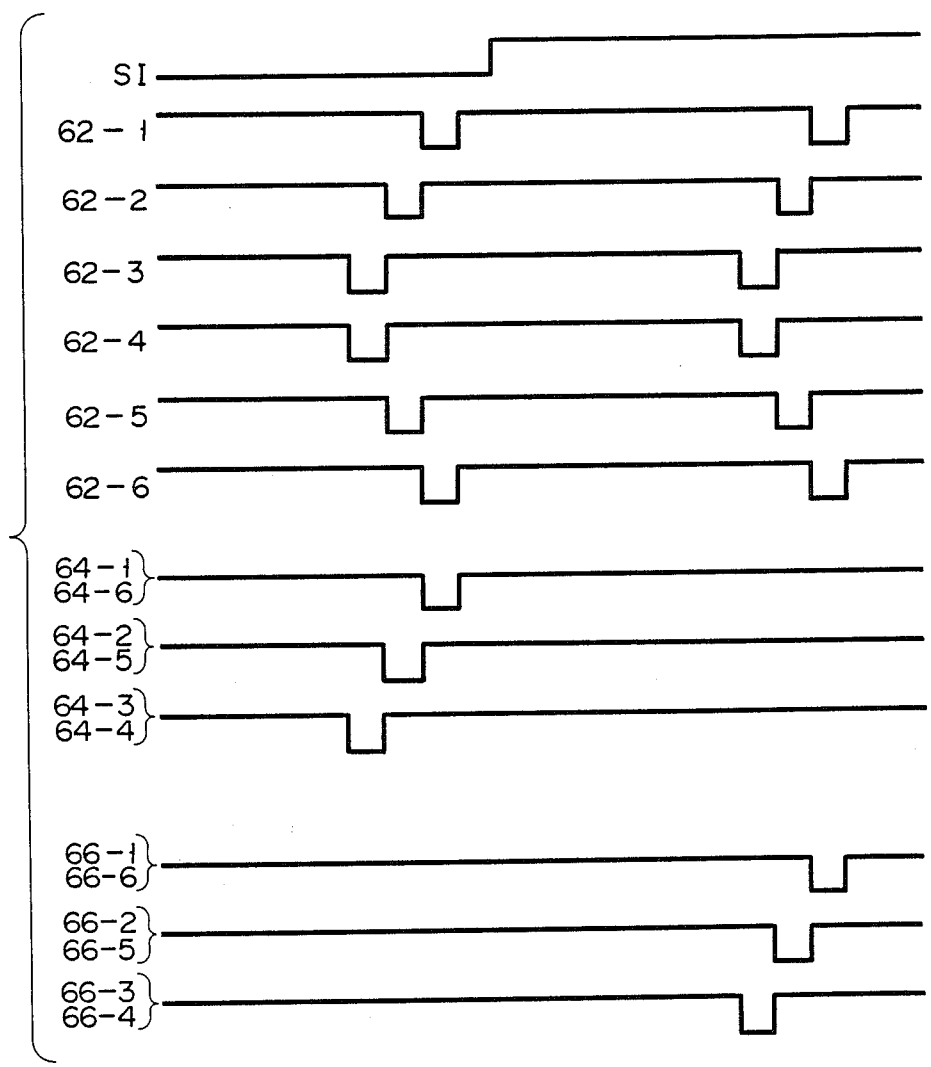
FIG. 6 is a timing chart for explaining an operation of the switching circuit of FIG. 5.

Since a voltage across the node between resistor Ra and photocoupler 40 is at high level, OR gate 46 is always enabled because one of its input terminals is at high level, and its output signal (c) becomes a signal which is always at high level as shown in FIG. 3C. Since one of the input terminals of OR gate 48 is at low level, OR gate 48 is enabled in response to rate pulse RP (shown in FIG. 3B) supplied to the other input terminal thereof, and rate pulse RP itself appears as its output signal (d) as shown in FIG. 3D. For this reason, circuit 28 supplies a drive signal (pulse signal) to transducer 16 in synchronism with rate pulse RP. A pulse width of the drive pulse corresponds to a resonance frequency of the ultrasonic transducer. Since rate pulse RP is not supplied to circuit 26, circuit 26 does not supply the drive signal to transducer 14. For this reason, when switch 30 is open, only transducer 16 generates ultrasonic pulses.

On the other hand, in order to select transducer 14, switch 30 is closed. When switch 30 is kept closed, photodiode 42 is turned on, photocoupler 40 is turned on, and signal (a) supplied to diagnostic device 34 goes to low level as shown in FIG. 3A. Therefore, device 34 displays, in accordance with this signal (a), that transducer 14 is selected. Since a voltage across the node between resistor Ra and photocoupler 40 is at low level, OR gate 48 is always enabled, and its output signal (d) becomes a signal which is always at high level as shown in FIG. 3D. OR gate 46 is enabled in response to rate pulse RP shown in FIG. 3B, and rate pulse RP itself appears as its output signal (c) as shown in FIG. 3C. Therefore, circuit 26 supplies the drive signal to transducer 14 in synchronism with rate pulse RP. For this reason, when switch 30 is kept closed, only transducer 14 generates ultrasonic pulses.

As described above, according to the first embodiment, the drive signal can be supplied to only one of transducers 14 and 16 by operating switch 30, i.e., the two transducers are not simultaneously driven. Therefore, unlike in a conventional apparatus, interference caused by a reflected wave of an ultrasonic wave transmitted from the other transducer having a different resonance frequency does not occur. In addition, close and remote images with high resolution can be obtained without decreasing a frame rate. Furthermore, since transmitting circuits for generating special drive signals for the respective transducers having different resonance frequencies are used, sensitivity is not degraded. Moreover, since a high-voltage drive signal is not switched but a transmitting circuit to be supplied with a rate pulse is switched on the TTL level, neither high-voltage or a large current switching element are required. Since the selection is performed by relay box 24 connecting diagnostic device 34 and probe 12, the same monitor of diagnostic device 34 can be used for all the probes having transducers with different resonance frequencies.

FIG. 4 is a circuit diagram of a modification of switching circuit 32 of the first embodiment. In this modification, one IC 54 and four switches S1, S2, S3, and S4 are provided. As IC 54, a TTL-PROM or a gate array is used. Rate pulse 56 input to IC 54 is selectively output to output terminals 01 to 04 in accordance with a combination of ON/OFF states of switches S1, S2, S3, and S4. Terminals 01 to 04 are respectively connected to transmitting circuits.

FIG. 5 is a circuit diagram of a second modification of switching circuit 32 of the first embodiment. In FIG. 1, the ultrasonic transducer is mechanically radial-scanned. However, in this modification, one transducer consisting of six elements is electronically sector- or linear-scanned, and this sector- or linear-scanning operation is switched by a programmable element such as a gate array 60. Three sets of 6-element output terminals 62-1 to 62-6, 64-1 to 64-6, and 66-1 to 66-6 are provided in array 60. A control signal of low level is first input to switching input terminal SI of array 60 from switch 30 and then the control signal of high level is input thereto. When terminal SI is at low level, outputs (rate pulses) are obtained from terminals 62-1 to 62-6 and 64-1 to 64-6, so that the transmitting circuit is operated and the ultrasonic pulse is transmitted from the transducers associating the first and second set. When terminal SI goes to a high level, outputs are obtained from terminals 62-1 to 62-6 and 66-1 to 66-6, so that the transmitting circuit is operated and the ultrasonic pulse is transmitted from the transducers associating the first and third set.

Therefore it is possible to switch the set of transducers to an electrical sector- or linear-scan type.

FIG. 7 is a circuit diagram of a second embodiment of the present invention. In FIG. 7, first and second ultrasonic transducers 72 and 74 having different ultrasonic characteristics, e.g., resonance frequencies, are connected to receiver/amplifier 78 through switching circuit 76. Ultrasonic lenses (not shown) having different focal lengths are mounted on transducers 72 and 74, respectively. Assume that transducers 72 and 74 are mechanically radial-scanned.

First and second transmitting circuits 80 and 82 for generating drive signals (pulse signals) having frequencies (pulse widths) respectively corresponding to the resonance frequencies of transducers 72 and 74 are connected to switching circuit 76. Circuits 80 and 82 are also connected to transmission selection circuit 84. Circuits 76 and 84 are connected to transducer selection switch 86 and selected thereby. Receiver/amplifier 78 and circuit 84 are connected to diagnostic device 88. Rate pulses are supplied to circuits 80 and 82 through circuit 84 from device 88. A reflected echo signal from one of transducers 72 and 74 selected by circuit 76 is input to device 88 through receiver/amplifier 78. Note that switch 86 supplies to device 88 a signal for displaying a resonance frequency of the currently selected transducer.

Figure 8:
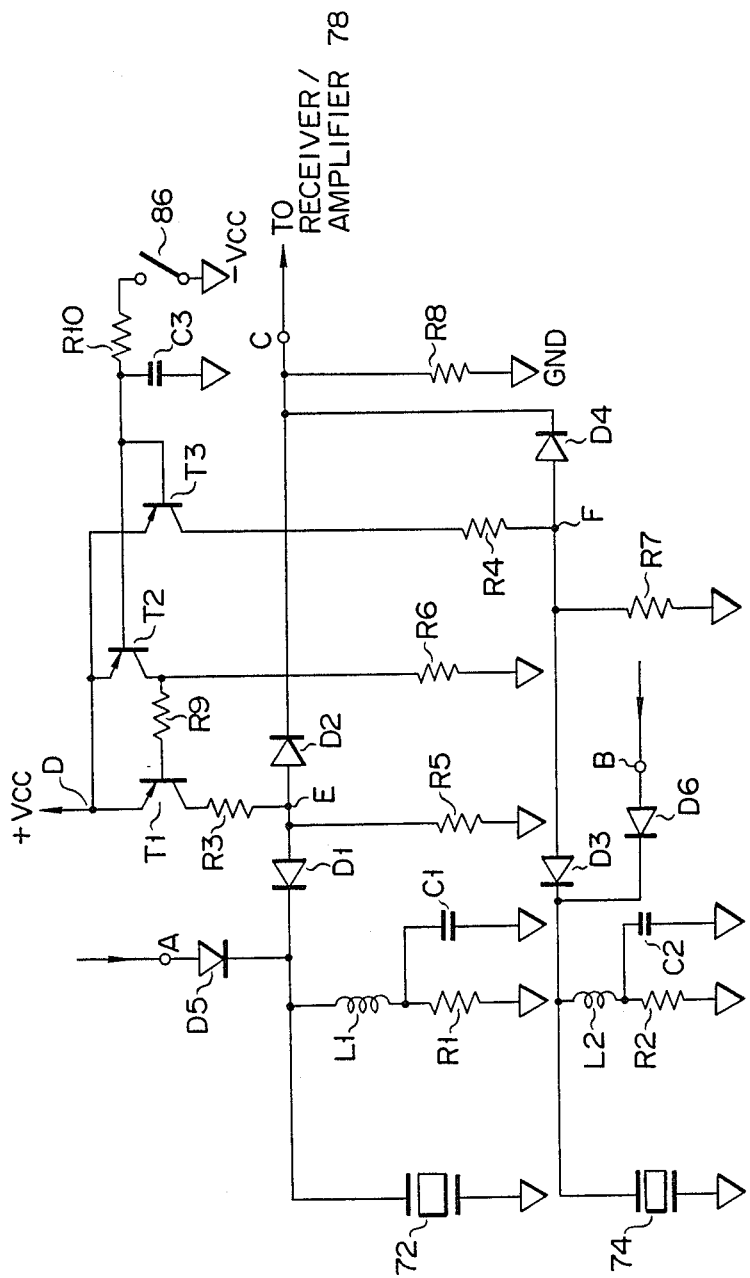
FIG. 8 is a circuit diagram of a switching circuit of the second embodiment.
Figure 9:
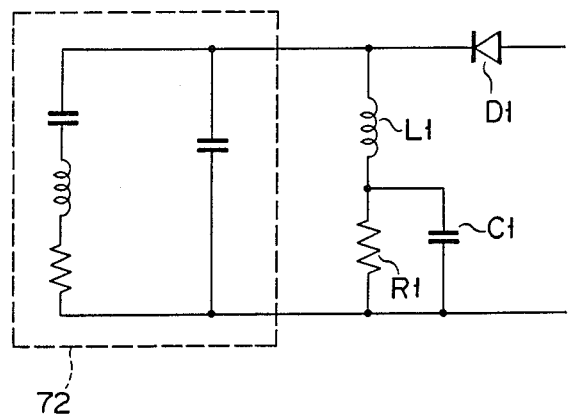
FIG. 9 is a circuit diagram for explaining matching between a transducer and the switching circuit of the second embodiment.

FIG. 8 is a circuit diagram of circuit 76 of the second embodiment shown in FIG. 7. Diode switching circuits are provided in circuit 76 respectively for transducers 72 and 74, and are switched by a transistor circuit. Therefore, an echo signal from one of the transducers is supplied to receiver/amplifier 78.

Diode switching circuits D1 and D2 are connected to transducer 72, and diode switching circuits D3 and D4 are connected to transducer 74. Transistors T1, T2, and T3 are connected to diodes D1 and D2, and D3 and D4. Switch 86 is connected to transistors T1, T2, and T3. Input terminal A and B receive drive signals having optimal pulse widths for transducers 72 and 74 from circuit 84. Actually, a drive signal for only one of transducers 72 and 74 selected by switch 86 is supplied.

In order to select transducer 72, switch 86 is opened. When switch 86 is open, capacitor C3 connected to the bases of transistors T2 and T3 is charged by a current flowing through a p-n junction between the emitter-base path of transistors T2 and T3, and the bases of transistors T2 and T3 are nearly equal to power source voltage Vcc as a voltage across node D. Therefore, transistors T2 and T3 are reverse-biased and turned off. Since the collector of transistor T3 is grounded through resistor R4, diode D3, inductor L2, and resistor R2, and through resistors R4 and R7, node F (the collector of transistor T3) is grounded.

Since transistor T2 is turned off, its collector voltage is grounded. As a result, a forward bias is applied to the base of transistor T1 through resistors R6 and R9, so that transistor T1 is turned on.

Assuming that resistor R5>>resistor R8=resistor R1 and that an ON resistance of transistor T1 is small enough, a voltage across node E between diodes D1 and D2 is determined by a current flowing through resistor R3, diode D2, inductor L1, and resistor R1, and through resistor R3, diode D2, and resistor R8 and is set at such a voltage that applies a forward bias to diodes D1 and D2.

When switch 86 is open, a drive signal is supplied to only terminal A, and no drive signal is supplied to terminal B. Since the forward bias is applied to diodes D1 and D2, the drive signal input to terminal A is supplied to transducer 72, an ultrasonic pulse is transmitted from transducer 72, and a reflected echo signal received by transducer 72 is output from output terminal C and supplied to receiver/amplifier 78. The reflected echo signal is amplified to a predetermined level and displayed as an ultrasonic tomographic image on device 88.

In this case, since node F is at ground level and node E is at positive level in terms of a DC potential, a reverse bias is applied to diode D4 and diodes D3 and D4 are turned off. As a result, if the reflected echo signal is received by transducer 74, a received signal from transducer 74 does not appear at terminal C.

In order to select transducer 74, switch 86 is closed. At this time, a drive signal is supplied to only terminal B, and no drive signal is supplied to terminal A. When switch 86 is closed, the bases of transistors T2 and T3 are grounded through resistor R10. Therefore, transistors T2 and T3 are forward-biased and turned on. Forward bias voltages are applied to diodes D3 and D4. As a result, the drive signal input to node B is supplied to transducer 74, an ultrasonic pulse is transmitted from transducer 74, and a reflected echo signal received by transducer 74 is output from terminal C and supplied to receiver/amplifier 78. In this case, since transistor T2 is turned on, a voltage across the node between resistors R6 and R9 becomes a voltage obtained by subtracting a voltage drop caused by an ON resistance of transistor T2 from voltage Vcc (i.e., a voltage across node D). Therefore, transistor T1 is reverse-biased and is turned off. Since a voltage across node E is a ground voltage, diodes D1 and D2 are reverse-biased, and the echo signal received by transducer 72 is not output to terminal C.

Inductors L1 and L2, resistors R1 and R2, and capacitors C1 and C2 at the cathode sides of diodes D1 and D3 respectively serve as matching circuits for the transducers and the switching circuit.

Figure 10A:
FIGS. 10A and 10B are views of ultrasonic waveforms of the second embodiment.
Figure 10B:

According to the second embodiment, the reflected echo signal appearing at terminal C becomes as shown in FIG. 10A, i.e., differs from that obtained in a conventional case shown in FIG. 10B (wherein the two transducers are simultaneously driven and outputs therefrom are simultaneously processed), thereby preventing mixing of noise.

Thus, according to the second embodiment, the received signal from the transducer other than the selected one can be prevented from being mixed. In addition, an arrangement of the receiver/amplifier is simplified, and an image with high quality without noise can be obtained.

As a modification of the second embodiment, if diodes D1, D2, D3, and D4 having high reverse withstand voltage are used, an echo signal from the nonselected transducer can not be supplied to receiver/amplifier 78 even if the two transducers simultaneously transmit ultrasonic pulses. Therefore, transmitting circuits 80 and 82 need not be switched. That is, transmission selection circuit 84 need not be provided.

In this embodiment, resonance frequencies and focal lengths of the two transducers are different from each other. However, only the focal lengths are different with the same resonance frequency, or vice versa. In addition, the number of the transducers is not limited to two but may be increased. Transducer selection switch 86 may be provided to the diagnostic device or to the probe.

In the first and second embodiments, although the two transducers are time-divisionally driven, transmitting circuits are respectively provided for them. A third embodiment using a common transmitting circuit will be described below. In the third embodiment, as in the above embodiments, a plurality of ultrasonic transducers which are all (through full 360 degrees rotation) scanned are provided in a probe and electrically selected. Therefore, the ultrasonic transducers can be advantageously selected without switching the probe in accordance with an object to be examined. However, a plurality of probes including ultrasonic transducers having different resonance frequencies and focal lengths may be provided, and the ultrasonic transducers may be selected by switching the probes in accordance with the object to be examined. As the third embodiment, a description will be made with reference to an ultrasonic endoscope apparatus in which a plurality of ultrasonic transducers which are integrally scanned are incorporated in the distal end of an insertion portion of an endoscope.

FIG. 11 is a block diagram of the third embodiment of the present invention. In FIG. 11, two ultrasonic transducers (piezoelectric elements) 112 and 114 having different resonance frequencies and focal lengths are fixed on transducer fixing member 116. Fixing member 116 is rotated by motor 118 at an end portion opposite to that where transducers 112 and 114 are fixed. Therefore, transducers 112 and 114 are rotated through a full 360 degrees. Fixing member 116 is inserted in an insertion portion of an endoscope and radial-scans an object to be examined. Transducers 112 and 114 are fixed at different positions in a circumference direction of fixing member 116 and hence are rotated with a predetermined phase difference (e.g., 180°).

Rotary encoder 120 is connected to motor 118, and an output from encoder 120 is supplied to encoder controller 122. Encoder 120 generates pulses in synchronism with rotation of motor 118, e.g., 256 sync. pulses for each rotation. A rotational speed of motor 118 is controlled by controller 122. Controller 122 generates pulses (512 pulses/revolution) at leading and trailing edges of the sync pulse supplied from encoder 120 and supplies them as a timing signal (rate pulses RP) for vibrating the transducer to diagnostic device 124. Encoder controller 122 also supplies a positioning pulse for positioning a display start position on a monitor screen to device 124.

Device 124 supplies a drive pulse synchronized with the timing signal to transmitting circuit 128 through switch 126. Switch 126 is manually operated and supplies the drive pulse from device 124 to transmitting circuit 128 through one of the first and second output terminals. Circuit 128 boosts the pulse voltage and supplies it to one of transducers 112 and 114 selected by switch 126.

The ultrasonic pulse transmitted from transducer 112 or 114, reflected on a boundary surface between tissues having different acoustic impedances, and received by transducer 112 or 114 again, is converted into a received signal and supplied to device 124 through amplifier 130. Device 124 modulates brightness of the received signal and displays a tomographic image of the object to be examined on the monitor.

When switch 126 is operated, the positioning pulse for positioning the display start position on the screen is moved by controller 122. Therefore, the display start position on the screen of the monitor of device 124 changes, so that a positional relationship of the object to be examined with respect to the transducers does not change on the monitor even if the ultrasonic transducers are switched to change a rotational phase.

The drive pulse generated from device 124 has a constant pulse width, and pulse widths of the drive pulses required for transducers 112 and 114 are different in accordance with their resonance frequencies. For this reason, before outputting the drive pulses supplied from device 124 to transducers 112 and 114 through switch 126, transmitting circuit 128 adjusts the pulse widths to obtain pulse widths corresponding to the resonance frequencies of transducers 112 and 114.

For this reason, differential circuits having time constants CR as shown in FIG. 12A are provided in circuit 128 for each transducer. By adjusting a value of time constant CR, a pulse width of output pulse Vout can be adjusted. That is, the differential circuits having time constants CR for obtaining pulse widths suitable for the resonance frequencies of transducers 112 and 114 are connected to transducers 112 and 114, respectively, and first and second outputs from switch 126 are respectively supplied to the differential circuits. That is, one of the differential circuits is selected by switch 126, and the pulse width of the drive pulse is converted into a pulse width corresponding to the resonance frequency. Actually, as shown in FIG. 12B, the drive pulse is supplied to the differential circuits through transformer 132.

When the pulse width of the drive pulse corresponds to the resonance frequency of the ultrasonic transducer as described above, vibration in a mode other than the required vibration mode in the direction of thickness can be reduced.

In general, it takes a long time to stop mechanical vibrations (corresponding to an application voltage curve) of the ultrasonic transducer (see FIGS. 14A and 14B). However, since electrical energy is efficiently converted into mechanical energy at resonance frequency $f_O$ (see FIG. 13), vibrations can be attenuated faster. For this reason, when an image is displayed on the monitor device, the voltage of the transducer drops to 0 faster and is kept 0 until the next drive pulse is input, i.e., not adversely affected by another pulse, thereby improving resolution of a displayed image of the object to be examined.

As described above, according to the third embodiment, when the ultrasonic transducers are switched, the time constants of the differential circuits are switched in accordance therewith, so that the pulse width of the drive pulse output from device 124 can be converted into an optimal pulse width corresponding to the resonance frequency of the selected ultrasonic transducer. Therefore, a pulse signal loss can be reduced, the resolution of the monitor device can be improved, thereby efficiently driving the ultrasonic transducers. For this reason, when the transducers are switched in accordance with the object to be examined, the same drive pulse generator as described above can be used.

A modification of transmitting circuit 128 of the third embodiment will be described. In a modification shown in FIG. 15, monostable multivibrator 150 is used as a pulse width converting means. Multivibrator 150 changes a pulse width of an output pulse by changing a resistance of variable resistor R' externally connected thereto. Therefore, the drive pulse having the pulse width corresponding to the resonance frequency of the ultrasonic transducer can be obtained, and the effect similar to that of FIG. 11 can be obtained.

In FIG. 16, a plurality of probes including ultrasonic transducers having different resonance frequencies are provided, and the probes are switched to switch the ultrasonic transducers. A drive pulse from a diagnostic device is supplied to input terminal Vin of PROM 160. Switch 162 is connected to PROM 160, and the drive pulse is output from one of the output terminals by operating switch 162. A plurality of monostable multivibrators 164 having different time constants are respectively connected to the output terminals of PROM 160. Outputs from multivibrators 164 are supplied to the ultrasonic transducers through open collector transistors 166. That is, since the drive pulses are converted into pulses having different pulse widths by operating switch 162, multivibrators 164 can be selected by operating switch 162 even if the probes are switched and the resonance frequency of the ultrasonic transducer is changed. In addition, when a signal supplied from PROM 160 to multivibrators 164 is selected from a plurality of signals, the third embodiment can be applied to the case wherein a plurality of transducers having different resonance frequencies are driven.

As described above, according to the third embodiment, the pulse width of the drive pulse is converted into a pulse width corresponding to the resonance frequency of the ultrasonic transducer and then supplied to the transducer. Therefore, driving efficiency can be improved, a pulse signal loss during signal transmission is reduced to attenuate mechanical vibrations faster, thereby providing an ultrasonic transducer with high resolution.

Note that the present invention is not limited to the above embodiments, but can be variously modified without departing from the spirit and scope of the present invention. For example, an application of the present invention is not limited to an ultrasonic endoscope, and an operation of the monitor device is not limited at all.

What is claimed is:

1. An ultrasonic diagnostic apparatus comprising:
   a plurality of transducer means scanned in a predetermined cycle and having different resonance frequencies;
   drive pulse generating means for periodically generating a drive pulse having a constant pulse width in synchronism with scanning of said ultrasonic transducer means;
   pulse width adjusting means for adjusting a pulse width of the drive pulse in accordance with a resonance frequency of a selected one of said ultrasonic transducer means, to apply it to said selected one of said ultrasonic transducer means;
   means for amplifying an echo signal from said transducer means;
   means for A/D converting the amplified echo signal and writing the converted signal in a memory provided in a diagnostic device;
   means for reading out data from the memory in accordance with an operation of display means; and
   means for D/A converting and displaying the readout data.

2. An apparatus according to claim 1, in which said pulse width adjusting means comprises a differential circuit.

3. An apparatus according to claim 1, in which said pulse width adjusting means comprises a monostable multivibrator.

4. An ultrasonic endoscope apparatus comprising:
   an endoscope having an endoscope main body including an insertion portion and a hand operating portion, and a plurality of ultrasonic transducer means provided at the distal end of said insertion portion and having different resonant frequencies;
   scanning means for changing directions of ultrasonic waves transmitted from said plurality of ultrasonic transducer means;
   selecting means for selecting one of said plurality of ultrasonic transducer means; and
   signal processing means for applying a drive signal corresponding to the resonant frequency of a selected one of said ultrasonic transducer means to only said selected one of said ultrasonic transducer means and for processing a received signal from only said selected one of said ultrasonic transducer means;
   means for generating a signal representing a reference position to display an image upon selection of said transducer means.

5. An ultrasonic diagnostic apparatus comprising:
   a plurality of ultrasonic transducer means (14,16) having different resonant frequencies;
   transmitting means (24), connected to said ultrasonic transducer means, for supplying a drive signal to only a selected one of said ultrasonic transducer means, said transmitting means including means for generating a rate pulse, a plurality of drive pulse generating means (26, 28) respectively connected to said ultrasonic transducer means, for applying drive pulses to said ultrasonic transducer means, in accordance with the rate pulse, the drive pulses corresponding to the resonant frequency of the plurality of ultrasonic transducer means, respectively and switching means for supplying the rate pulse to one of said plurality of drive pulse generating means;
   receiving means (76, 78), connected to said ultrasonic transducer means, for processing a received signal from only said selected one of said ultrasonic transducer means, to generate an image signal; and
   reference signal generating means for generating a reference signal for displaying an image.

* * * * *